(12) United States Patent
Takeda et al.

(10) Patent No.: US 7,332,289 B2
(45) Date of Patent: Feb. 19, 2008

(54) METHOD OF PURIFYING PROTEIN

(75) Inventors: Kozo Takeda, Tokyo (JP); Norimichi Ochi, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 511 days.

(21) Appl. No.: 10/471,374

(22) PCT Filed: Mar. 11, 2002

(86) PCT No.: PCT/JP02/02248

§ 371 (c)(1),
(2), (4) Date: Sep. 9, 2003

(87) PCT Pub. No.: WO02/072615

PCT Pub. Date: Sep. 19, 2002

(65) Prior Publication Data

US 2004/0138424 A1  Jul. 15, 2004

(30) Foreign Application Priority Data

Mar. 9, 2001  (JP) ............................. 2001-067111

(51) Int. Cl.
*G01N 33/53*  (2006.01)
(52) U.S. Cl. ..................... 435/7.1; 435/6; 435/7.2; 435/7.92; 435/69.1
(58) Field of Classification Search ............ 435/6, 435/7.1, 7.2, 7.92, 69.1
See application file for complete search history.

(56) References Cited

U.S. PATENT DOCUMENTS 5,777,085 A * 7/1998 Co et al. ............... 530/388.23
5,808,033 A * 9/1998 Gourlie et al. ............ 536/23.53
6,406,909 B1 * 6/2002 Shibuya et al. ............. 435/404
6,903,194 B1 * 6/2005 Sato et al. ............... 530/387.1

FOREIGN PATENT DOCUMENTS

| EP | 0 089 218 A2 | 9/1983 |
| EP | 0 168 506 A1 | 1/1986 |
| EP | 0 537 148 A1 | 4/1993 |
| EP | 0 962 467 A1 | 8/1999 |
| EP | 997152 | 5/2000 |
| EP | 1 020 522 A1 | 7/2000 |
| JP | 11-092399 A | 4/1999 |
| JP | 11-98997 A | 4/1999 |
| WO | WO 91/18919 | 12/1991 |
| WO | WO 92/07084 | 4/1992 |

OTHER PUBLICATIONS

Robert Lydersen et al., Acid precipitation of mammlian cell fermentation broth, journal, Nov. 30, 1994, 10 pp., vol. 745 XP009033271, Annals of the New York Academy of Sciences, United States.

Hirofumi Shinkura et al., Safety and Kinetic properties of a humanized antibody to human interleukin-6 receptor in healthy non-human primates, abstract, Oct. 19, 1997, 8 pp., 163-170 XP001069948, Toxicology.

* cited by examiner

*Primary Examiner*—Long V. Le
*Assistant Examiner*—Jacob Cheu
(74) *Attorney, Agent, or Firm*—Browdy and Neimark, PLLC

(57) ABSTRACT

A method for removing contaminant DNA in a sample containing a physiologically active protein, which comprises the following steps:
1) converting the sample containing a physiologically active protein into a neutral aqueous solution of low conductivity; and
2) removing the resulting particles.

13 Claims, No Drawings

METHOD OF PURIFYING PROTEIN

TECHNICAL FIELD

The present invention relates to a method for purifying proteins, more specifically to a method for removing contaminant DNA from a sample containing a physiologically active protein such as antibody molecules.

BACKGROUND ART

Advances in gene recombinant technology have enabled the provision of a stable supply of various protein formulations. In particular, a variety of recombinant antibody drugs, which are more selective than normal-drugs, have been developed and entered clinical trial in recent years.

In these recombinantly produced formulations containing physiologically active proteins, there is a need to remove host DNA and contaminant DNA associated with viral contamination. Under present World Health Organization (WHO) criteria, the amount of DNA in biological drugs should not exceed 100 pg DNA/dose. To meet this criteria, in general, an aqueous medium containing a physiologically active protein obtained from host cells is treated by anion-exchange chromatography, hydroxyapatite chromatography or a combination thereof for the purpose of removing DNA.

In particular, in a case where a physiologically active protein is an antibody produced recombinantly in mammalian host cells, the aqueous medium is treated by affinity column chromatography on Protein A or Protein G before purification by various types of chromatography, based on the binding property of Protein A or Protein G to IgG Fc chain.

By way of example, in JP 5-504579 A, an antibody-containing aqueous medium obtained from mammalian cell culture is applied to Protein A/G column chromatography to adsorb antibody molecules onto the column, and is then eluted with an acidic solution (about 0.1 M citric acid, pH 3.0-3.5) to release the antibody molecules. The resulting acidic eluate is sequentially applied to ion-exchange column chromatography and size exclusion column chromatography to give the purified antibody molecules.

However, these individual chromatographic processes and a combination thereof are time-, labor- and cost-consuming, as well as being complicated. Moreover, they fail to provide stable results.

Thus, there is a need to develop a simpler and less expensive method for purifying physiologically active proteins, especially antibodies, which can ensure removal of contaminant DNA, and which can minimize a loss of physiologically active proteins.

DISCLOSURE OF THE INVENTION

As a result of extensive and intensive efforts made to overcome these problems, the inventors of the present invention have made the surprising finding that contaminant DNA can be efficiently removed from a sample containing a physiologically active protein without using complicated chromatographic processes in a case where the sample is converted into an acidic aqueous solution of low conductivity, neutralized by addition of a buffer to raise the pH to a neutral level, and then filtered through a filter to remove the resulting particles. This finding led to the completion of the present invention.

Namely, the present invention provides the following:
(1) A method for removing contaminant DNA in a sample, containing a physiologically active protein, which comprises the following steps:
   1) converting the sample containing a physiologically active protein into a neutral aqueous solution of low conductivity; and
   2) removing the resulting particles.
(2) A method for removing contaminant DNA In a sample containing a physiologically active protein, which comprises the following steps:
   1) converting the sample containing a physiologically active protein into an acidic or alkaline aqueous solution of low conductivity;
   2) adjusting the pH of the resulting sample to a neutral level; and
   3) removing the resulting particles.
(3) A method for removing contaminant DNA in an antibody-containing sample, which comprises the following steps:
   1) applying the antibody-containing sample to affinity chromatography on Protein A or Protein G to elute the antibody with an acidic aqueous solution of low conductivity;
   2) neutralizing the resulting eluate by addition of a buffer to raise the pH to a neutral level; and
   3) removing the resulting particles.
(4) The method according to (2) or (3) above, wherein the acidic aqueous solution of low conductivity has a molarity of 0 to 100 mM.
(5) The method according to (2) or (3) above, wherein the acidic aqueous solution of low conductivity has an ionic strength of 0 to 0.2.
(6) The method according to (2) or (3) above, wherein the acidic aqueous solution of low conductivity has a conductivity of 0 to 300 mS/m.
(7) The method according to any one of (2) to (6) above, wherein the acidic aqueous solution is selected from aqueous solutions of hydrochloric acid, citric acid and acetic acid.
(8) The method according to (7) above, wherein the acidic aqueous solution has a pH of 1.5 to 3.9.
(9) The method according to any one of (1) to (7) above, wherein the contaminant DNA is present at a DNA concentration of 22.5 pg/ml or less in the treated sample containing a physiologically active protein.
(10) The method according to (3) above, wherein the buffer is an aqueous solution of Tris.
(11) The method according to (3) above, wherein the buffer is added to raise the pH to 4.3 to 7.5.
(12) The method according to (1) or (2) above, wherein the physiologically active protein is an antibody.
(13) The method according to (3) or (12) above, wherein the antibody is a humanized monoclonal antibody.
(14) The method according to (13) above, wherein the antibody is a humanized anti-IL-6 receptor antibody.
(15) The method according to (13) above, wherein the antibody is a humanized anti-HM1.24 antigen monoclonal antibody.
(16) The method according to (13) above, wherein the antibody is a humanized anti-parathyroid hormone-related peptide antibody (anti-PTHrP antibody).
(17) The method according to (13) above, wherein the antibody is a humanized anti-tissue factor antibody.
(18) The method according to any one of (1) to (3) above, wherein the particles are removed by filtration through a filter.

(19) A purified physiologically active protein obtainable by the method according to (1) or (2) above.
(20) A purified antibody obtainable by the method according to (3) above.
(21) A purified antibody substantially free from antibody-DNA conjugates in a neutral aqueous solution of low conductivity.
(22) A purified antibody having a DNA concentration of 22.5 pg/ml or less.

BEST MODE FOR CARRYING OUT THE INVENTION

Examples of a physiologically active protein contained in a sample to be purified by the method of the present invention include, but are not limited to, hematopoietic factors such as granulocyte colony-stimulating factor (G-CSF), granulocyte-macrophage colony-stimulating factor (GM-CSF), erythropoietin (EPO) and thrombopoietin, cytokines such as interferons, IL-1 and IL-6, monoclonal antibodies, tissue plasminogen activator (tPA), urokinase, serum albumin, blood coagulation factor VIII, leptin, insulin, and stem cell growth factor (SCF). Among these proteins, preferred are EPO, G-CSF and antibodies including monoclonal antibodies, and more preferred are monoclonal antibodies. In an embodiment of the present invention using Protein A/G affinity chromatography, monoclonal antibodies are preferred for purification.

A "physiologically active protein" refers to a protein having substantially the same biological activities as a physiologically active mammalian (especially, human) protein. Such a protein may be naturally-occurring or recombinant, preferably recombinant. A recombinant protein encompasses those having the same amino acid sequence as the corresponding native protein, as well as those comprising deletion, substitution or addition of one or more amino acids in the amino acid sequence, but retaining the biological activities as mentioned above. Further, a physiologically active protein as used herein includes those chemically modified with PEG, etc.

When a physiologically active protein is a glycoprotein, it may be glycosylated with sugar chains of any origin, preferably of mammalian origin. Mammalian cells capable of glycosylation include, for example, Chinese hamster ovary (CHO) cells, BHK cells, COS cells and human-derived cells, with CHO cells being most preferred.

When a physiologically active protein is EPO, it may be prepared in any manner, for example, by extraction from human urine in various manners or by recombinant production in Chinese hamster ovary (CHO) cells, BHK cells, COS cells, human-derived cells or the like (e.g., as described in JP 61-12288 A). EPO thus prepared is isolated and purified In various manners before use in the present invention. In addition, EPO may be chemically modified with PEG, etc. (see WO90/12874). EPO as used herein further includes unglycosylated EPO that Is chemically modified with PEG, etc. Likewise, EPO analogs are also included, which are modified to have at least one additional site for N-linked or O-linked glycosylation in the amino acid sequence of EPO (see, e.g., JP 8-151398 A, JP 8-506023 A). Instead of increasing the number of glycosylation sites, EPO analogs may also be modified to have an increased content of sialic acid or the like for attaining additional sugar chains.

When a physiologically active protein is G-CSF, any G-CSF can be used as long as it is highly purified. G-CSF as used herein may be prepared in any manner, for example, by extraction from cultured human tumor cell lines or by recombinant production in bacterial cells such as E. coli; yeast cells: or animal-derived cultured cells such as Chinese hamster ovary (CHO) cells, C127 cells or COS cells. G-CSF thus prepared is isolated and purified in various manners before use in the present invention. Preferred is a recombinant G-CSF produced in E. coli, yeast cells or CHO cells. The most preferred is a recombinant G-CSF produced in CHO cells. In addition, G-CSF may be chemically modified with PEG, etc. (see WO90/12874).

When a physiologically active protein is a monoclonal antibody, it may be prepared in any manner. A monoclonal antibody can be produced, in principle, using known techniques by immunizing a sensitized antigen in a standard manner for immunization, fusing the resulting immunocytes with known parent cells in a standard manner for cell fusion, and then screening monoclonal antibody-producing cells in a standard manner for screening. Further, a monoclonal antibody as used herein is not limited to those produced by hybridomas, but includes chimeric antibodies which are artificially modified, e.g., for the purpose of reducing xenoantigenicity to human. Alternatively, reshaped humanized antibodies may also be used in the present invention. Such antibodies are prepared by replacing complementarity-determining regions of human antibodies with those of non-human mammalian (e.g., mouse) antibodies; standard recombinant procedures for this purpose are also known. Such known procedures may be used to give reshaped humanized antibodies.

If necessary, amino acid substitutions may be made in the framework (FR) regions of antibody variable domains such that the complementarity-determining regions of reshaped humanized antibodies form appropriate antigen-binding sites (Sato, et al., Cancer Res. 53:1-6, 1993). A humanized anti-IL-6 receptor antibody (hPM-1) can be presented as a preferred example for such reshaped humanized antibodies (see WO92/19759). In addition to this, a humanized anti-HM1.24 antigen monoclonal antibody (see WO98/14580), a humanized anti-parathyroid hormone-related peptide antibody (anti-PTHrP antibody)(see WO98/13388), a humanized anti-tissue factor antibody (see WO99/51743) and the like are also preferred for use in the present invention.

Further, human antibodies produced in transgenic animals or by phage display technology etc. are also preferred.

As used herein, a "sample containing a physiologically active protein" or an "antibody-containing sample" preferably refers to a culture medium of mammalian cells (e.g., CHO cells) containing a physiologically active protein or antibody molecules produced by culture, which may further be subjected to partial purification or other specific treatment.

In a preferred embodiment of the present invention, contaminant DNA in a sample containing a physiologically active protein is removed by a method comprising the following steps:

1) converting the sample containing a physiologically active protein into a neutral aqueous solution of low conductivity; and 2) removing the resulting particles.

As used herein, a "neutral aqueous solution of low conductivity" generally refers to an-aqueous solution of pH 4 to pH 8, preferably of pH 4.5 to pH 7.5, which has a molarity of 0 to 100 mM, preferably 0 to 50 mM, more preferably 0 to 30 mM, or has an ionic strength of 0 to 0.2, preferably 0 to 0.12, or has a conductivity of 0 to 300 mS/m, preferably 0 to 200 mS/m, more preferably 0 to 150 mS/M.

In another preferred embodiment of the present invention, contaminant DNA in a sample containing a physiologically active protein is removed by a method comprising the following steps:

1) converting the sample containing a physiologically active protein into an acidic or alkaline aqueous solution of low conductivity;
2) adjusting the pH of the resulting sample to a neutral level; and
3) removing the resulting particles.

In yet another preferred embodiment of the present invention, which is very advantageous when a physiologically active protein is an antibody, contaminant DNA in an antigen-containing sample is removed by a method comprising the following steps:

1) applying the antibody-containing sample to affinity chromatography on Protein A or Protein G to elute the antibody with an acidic aqueous solution of low conductivity;
2) neutralizing the resulting eluate by addition of a buffer to raise the pH to a neutral level; and
3) removing the resulting particles.

In the method of the present invention, a sample containing a physiologically active protein is converted into an acidic aqueous solution of low conductivity, preferably by eluting the sample from Protein A/G affinity chromatography with an acidic aqueous solution of low conductivity. As used herein, an "acidic aqueous solution of low conductivity" generally refers to an aqueous solution of pH 1.5 to pH 3.9, preferably of pH 2.0 to pH 3.9, more preferably of pH 2.0 to pH 3.0, which has a molarity of 0 to 100 mM, preferably 0 to 50 mM, more preferably 0 to 30 mM, or has an ionic strength of 0 to 0.2, preferably 0 to 0.12, or has a conductivity of 0 to 300 mS/m, preferably 0 to 200 mS/m, more preferably 0 to 150 mS/m. The acidic aqueous solution may be selected from aqueous solutions of hydrochloric acid, citric acid, acetic acid and other acids. The type, conductivity and pH of acidic aqueous solution of low conductivity will vary depending on the type of physiologically active protein or antibody to be purified. Those skilled in the art will readily determine optimal conditions for these parameters in preliminary experiments as described herein.

In the method of the present invention, after a sample containing a physiologically active protein is converted into an acidic aqueous solution of low conductivity, the resulting sample is neutralized by addition of a buffer to raise the pH to a neutral level. Alternatively, an antibody-containing sample is applied to affinity chromatography on Protein A or Protein G, eluted with an acidic aqueous solution of low conductivity, and then neutralized by addition of a buffer to raise the pH to a neutral level. A buffer added at this stage includes, for example, Tris-HCl buffer and phosphate buffer, and further includes aqueous Tris solution, aqueous $Na_2HPO_4$ solution, aqueous NaOH solution, etc. A neutral level will vary depending on the type of physiologically active protein or antibody to be purified. It usually ranges from pH 4 to pH 8, preferably pH 4.3 to pH 7.5, and more preferably pH 4.5 to pH 7.5. Those skilled in the art will readily determine optimal conditions for the type of buffer used and a neutral pH level in preliminary experiments as described herein.

Likewise, an "alkaline aqueous solution of low conductivity," as used herein, generally refers to an aqueous solution of pH 7.5 to pH 13, which has a molarity of 0 to 100 mM, preferably 0 to 50 mM, more preferably 0 to 30 mM, or an ionic strength of 0 to 0.2, preferably 0 to 0.12, or has a conductivity of 0 to 300 mS/m, preferably 0 to 200 mS/m, more preferably 0 to 150 mS/m. The pH of this solution will vary depending on the type of physiologically active protein or antibody to be purified.

According to the present invention, the solution neutralized to a neutral pH level in the above stage, in turn, produces particles (i.e., becomes clouded). These particles may be removed by filtration through a filter to ensure efficient removal of contaminant DNA. Examples of a filter available for filtration include, but are not limited to, a 1.0-0.2 μm Cellulose Acetate Filter System (Corning) or TFF.

Alternatively, these particles may also be removed by centrifugation or any other techniques for efficient particle removal; procedures for removal are not limited to filtration through a filter.

Without being bound by any particular theory, the inventors of the present invention estimate that each of these particles is a conjugate formed between physiologically active protein and DNA. Particle removal by filtration results in a small loss of physiologically active protein because it is removed in the form of DNA-physiologically active protein conjugates. However, such a small loss constitutes only a few percent of the total amount of the physiologically active protein; about 90% of the physiologically active protein can be collected, as will be described in the Examples below.

The inventors of the present invention also estimate that Protein A/G column chromatography alone is not sufficient to ensure effective separation between contaminant DNA and physiologically active protein because DNA-protein conjugates are formed on the column resin.

The physiologically active protein thus purified is available for use as a pharmaceutical formulation after further purification by cation-exchange chromatography, anion-exchange chromatography, hydroxyapatite chromatography, or combinations thereof.

Quantitative DNA assay may be accomplished by, but not limited to, Threshold Total DNA assay along with DNA extraction prior to the assay.

The method of the present invention enables contaminant DNA to be efficiently removed in a very simple manner up to an extremely low DNA concentration (e.g., 22.5 pg/ml); it is significantly advantageous in purifying physiologically active proteins, especially antibody molecules. The method of the present invention also enables cost reduction and has great significance in this technical field.

The present invention will be further described in the following Examples, which are not intended to limit the scope of the invention. Based on the detailed description, various changes and modifications will be apparent to those skilled in the art, and such changes and modifications fall within the scope of the invention.

EXAMPLES

Example 1

Examination of Buffer Composition for Protein A Affinity Chromatography in Purifying hPM-1 (Humanized Anti-IL-6 Receptor Antibody)

(1) Test Material (Antibody-Containing Sample)

A sample containing the culture medium (hereinafter abbreviated as CM) of CHO cells producing hPM-1 antibody (humanized anti-IL-6 receptor antibody), which had been centrifuged to remove the cells and stored at −80° C., was filtered through a 0.22 μm Cellulose Acetate (abbreviated as CA) Filter-System (CORNING) and used as a test sample for purification examination. The hPM-1 antibody was prepared as described in Reference Example 2 of JP 8-99902 A using the human elongation factor Iα promoter shown in Example 10 of WO92/19759.

(2) Instrument Used for Examination

For HCl Eluate
HPLC: L-6200 Intelligent Pump (HITACHI)
   L-4200 UV-VIS Detector (HITACHI)
   D-2500 Chromato-Integrator (HITACHI)
Column: HR5/2 (Pharmacia), 5 mm I.D.×20 mmH
Media: POROS 50A (PerSeptive), 0.4 ml
   Lot; A250-039, Code; SPECIAL For Particles
HPLC: Waters PrepLC4000 System (Waters)
   Waters2000 System Controller (Waters)
   Waters486 Tunable Absorbance Detector (Waters)
   Waters741 Data Module (Waters)
Spectrophotometer: U-2000 (HITACHI)
Column: XK26 (Pharmacia), 26 mm I.D.×100 mmH
Media: POROS 50A (PerSeptive), 53 ml
   Lot; A250-039, Code; SPECIAL (3) Analysis and Assay
hPM-1 assay:
   hPM-1 is assayed by reversed-phase HPLC on a PLRP-S column (Polymer Laboratories) with a linear gradient.
DNA assay:
   DNA is measured by Threshold Total DNA assay. Prior to the assay, DNA extraction is performed (e.g., using a DNA extracter kit, Wako Pure Chemicals Industries, Ltd.). Likewise, a Threshold Total DNA assay kit (Molecular Devices) is used for the measurement.
Turbidimetry:
   Each test sample is monitored for particle formation by measuring its absorbance at 660 nm in a spectrophotometer U-2000 (HITACHI).

(1) Examination of Elution Conditions

By varying the buffer composition for elution in Protein A affinity chromatography, examination was performed to confirm % recovery of hPM-1 and DNA removal by elution. The above antibody-containing sample was applied to the column under the conditions indicated in Table 1 below. Protein A resin was equilibrated with the equilibration buffer indicated in Table 1 and then loaded with the above antibody-containing sample, followed by Washing 1, Washing 2 and elution. The elution profile was monitored at A280 nm to isolate a protein peak. In the table, C-P Buffer denotes citrate-phosphate buffer.

TABLE 1

|  | Elution method 1 | Elution method 2 | Elution method 3 |
|---|---|---|---|
| Equilibration | 1M NaCl/100 mM C-P Buffer, pH 7.5 | 1M NaCl/10 mM C-P Buffer, pH 7.5 | 1M NaCl/100 mM C-P Buffer, pH 7.5 |
| Washing 1 | 1M NaCl/100 mM C-P Buffer, pH 7.5 | 1M NaCl/10 mM C-P Buffer, pH 7.5 | 1M NaCl/100 mM C-P Buffer, pH 7.5 |
| Washing 2 | 100 mM C-P Buffer, pH 7.5 | 10 mM C-P Buffer, pH 7.5 | 100 mM C-P Buffer, pH 7.5 |
| Elution | 100 mM C-P Buffer, pH 2.6 | 2.5 mM HCl, pH 2.6 | 2.5 mM HCl, pH 2.6 |

No chromatographic difference was observed among Elution methods 1, 2 and 3.

Each elution fraction was adjusted to pH 7.0 with a 300 mM Tris solution, indicating that particles were generated in the fractions eluted with HCl (Elution methods 2 and 3). Further examination was performed to determine the correlation between particle formation and % recovery of hPM-1 or the amount of residual DNA.

To examine the particle correlation, the HCl eluate from Elution method 2 was supplemented with NaCl and analyzed for the correlation between the concentrations of NaCl added (0 mM, 50 mM, 100 mM) and various factors. To analyze the correlation between the concentrations of NaCl added and various factors, filtered and unfiltered samples were prepared as follows: each Protein A elution fraction supplemented with NaCl was adjusted to pH 7.0 with a 300 mM Tris solution and then filtered or unfiltered through a 0.22 μm CA Filter. The filtered and unfiltered samples were measured for % recovery of hPM-1 (filtered samples only) and the amount of residual DNA.

% Recovery

The % recovery of hPM-1 was measured for the individual elution methods. As a result, the % recovery was as high as 98.6% in Elution method 1. In contrast, the % recovery varied from 83.8% to 97.1% in Elution method 2 and from 83.5% tp 93.7% in Elution method 3; these variations were estimated to be due to the smallness of examination scale (resin volume: 0.4 ml). When the purification scale was increased, it was confirmed that the % recovery of hPM-1 was stabilized at 90% or more (Elution method 2). Thus, the % recovery of hPM-1 was also found to remain high even in HCl elution.

Correlation between the Concentrations of NaCl Added and Various Factors in the HCl Eluate Table 2 summarizes the analysis of the correlation between the concentrations of NaCl added and various factors in the HCl eluate.

TABLE 2

|  | concentration of NaCl added | | |
|---|---|---|---|
|  | 0 mM | 50 mM | 100 mM |
| Turbidity (pH unadjusted) | 0.004 | 0.007 | 0.011 |
| Turbidity (pH adjusted) | 0.252 | 0.049 | 0.020 |
| % Recovery of hPM-1 (filtered) (%) | 81 | 86 | 88 |
| Amount of DNA (unfiltered) (pg DNA/mg hPM-1) | 98 | 220 | 241 |
| Amount of DNA (filtered) (pg DNA/mg hPM-1) | 11 | 30 | 250 |

For the filtered samples, the % recovery of hPM-1 was 88% at 100 mM NaCl, 86% at 50 mM NaCl and 81% at 0 mM NaCl. The amount of residual DNA was low at 0 mM NaCl in both filtered and unfiltered samples. In particular, the filtered sample supplemented with 0 mM NaCl had a very low DNA content of 11 pg DNA/mg hPM-1.

The pH-adjusted samples with a higher turbidity tend to provide a lower % recovery of hPM-1 and a smaller amount of residual DNA after filtration. This result suggests a high possibility that hPM-1 and DNA both contribute to particle formation. It is estimated that hPM-1 and DNA probably interact with each other to form particles by adjusting the pH to 7.0. In relation to a higher % recovery of hPM-1, it is preferable to increase the NaCl concentration added to the HCl eluate. In relation to a decreased amount of residual DNA, on the other hand, it is desirable to eliminate NaCl supplementation into the HCl eluate.

Example 2

Purification of Humanized Anti-PTHrP Antibody

A sample containing a humanized anti-PTHrP antibody (a culture medium from CHO cell culture, filtered through 0.45 and 0.2 μm CA SARTOBRAN P filters (sartorius)) was purified by Protein A affinity column chromatography under the conditions indicated below. The anti-PTHrP antibody was prepared as described in WO98/13388.

Experimental Condition
Purification device: AKTA explorer (Amersham Pharmacia Biotech)
Column: HR5/5, C10, XK-26 (Amersham Pharmacia Biotech)
Resin: rProtein A Sepharose Fast Flow
Load: direct load of the culture medium (pH 6.6 to pH 7.5)
Adjustment of elution fraction: elution fractions are adjusted to various pH levels with a 1 M aqueous Tris solution and then filtered through a 0.2 μm Cellulose Acetate (hereinafter abbreviated as CA) to remove DNA (the conditions are examined in (1) below).

The Protein A column was sufficiently equilibrated with 150 mM NaCl-containing citrate-phosphate buffer (pH 7.5) and then loaded with the above antibody-containing CM. Subsequently, the column was washed with 150 mM NaCl-containing citrate-phosphate buffer (pH 7.5) to remove unbound impurities, further washed with citrate-phosphate buffer (pH 7.5) to decrease the conductivity, and then eluted with 20 mM aqueous citric acid. The elution profile was monitored at A280 nm to isolate a protein peak. This Protein A elution fraction was used for the following examination of conditions.

(1) Examination of Removal Conditions for Residual DNA In the Eluate

To ensure efficient removal of residual DNA, examination was performed to determine the optimal pH for filtration through a filter. The Protein A elution fraction was adjusted with a 1.0 M aqueous Tris solution to the following pH levels: 2.7 (unadjusted), 4.0, 4.5, 5.0, 5.5, 6.0, 6.5, 7.0 and 7.5. Subsequently, each sample was allowed to stand for a given period of time, filtered through a 0.22 μm CA filter, and then adjusted to pH 7 with a 1.0 M aqueous Tris solution, followed by DNA assay.

Table 3 lists the examined pH levels and standing periods, along with the amount of residual DNA.

As shown in the table, the amount of residual DNA was below the detection limit at pH 5.5 and pH 6.0 in all cases where the samples were allowed to stand for 0, 6 and 24 hours. Also, the removal of residual DNA reached a peak around pH 5.5 and pH 6.0, whereas decreased efficacy of DNA removal was observed at higher and lower pH levels.

Example 3

Purification of Humanized Anti-HM1.24 Antigen Monoclonal Antibody

A sample containing a humanized anti-HM1.24 antigen monoclonal antibody (a culture medium from CHO cell culture) was purified by Protein A affinity column chromatography under the conditions indicated in Table 4 below. The anti-HM1.24 antigen monoclonal antibody was prepared as described in WO98/14580.

Experimental Conditions
Column: rProtein A FF, 5 mL (16 mm ID×25 mmH)
Flow rate: 5 mL/min (150 cm/h)
Sample: direct load of the culture medium

TABLE 4

| | |
|---|---|
| Equilibration (20 CV) | 10 mM C-P Buffer, 1M NaCl, pH 7.5 |
| Load | Direct load of CM |
| Washing 1 (20 CV) | 10 mM C-P Buffer, 1M NaCl, pH 7.5 |
| Washing 2 (20 CV) | 10 mM C-P Buffer, pH 7.5 |
| Elution (10 CV) | Citric acid, pH 2.5 |
| Washing 3 (4 CV) | 0.1M NaOH |

The Protein A column was sufficiently equilibrated with 150 mM NaCl-containing citrate-phosphate buffer (pH 7.5) and then loaded with the above antibody-containing CM. Subsequently, the column was washed with 150 mM NaCl-containing citrate-phosphate buffer (pH 7.5) to remove unbound impurities, further washed with citrate-phosphate buffer (pH 7.5) to decrease the conductivity, and then eluted with 20 mM aqueous citric acid. The elution profile was monitored at A280 nm to isolate a protein peak. This Protein A elution fraction was used for the following examination of conditions.

To ensure efficient removal of residual DNA, examination was performed to determine the optimal pH for filtration through a filter. The Protein A elution fraction was adjusted with a 1.0 M aqueous Tris solution to the following pH levels (pH=4.5-7.5). Subsequently, each sample was allowed to stand for a given period of time, filtered through a 0.22 μm CA filter, and then adjusted to pH 7 with a 1.0 M aqueous Tris solution, followed by DNA assay and reversed-phase HPLC for assay of the humanized anti-HM1.24 antigen monoclonal antibody. Table 5 shows the results of DNA

TABLE 3

Removal of residual DNA (unit: pg/mL)

| | pH 7.5 | pH 7.0 | pH 6.5 | pH 6.0 | pH 5.5 | pH 5.0 | pH 4.5 | pH 4.0 | Direct (pH 2.7) |
|---|---|---|---|---|---|---|---|---|---|
| 0 hr. | 984 | 83.3 | 53.8 | <22.5 | <15.0 | 17.2 | 54.1 | 32,052 | 40,878 |
| 6 hr. | 816 | 51.9 | <15.0 | <22.5 | <15.0 | <15.0 | 44.0 | 38,172 | 42,078 |
| 24 hr. | 310 | 46.6 | <15.0 | <22.5 | <15.0 | <15.0 | 39.7 | 42,528 | 30,222 |

(DNA in the culture medium: 6,637,200 pg/mL; DNA in the unfiltered sample: 25,110 pg/mL)

assay, while Table 6 shows the yield of the humanized anti-HM1.24 antigen monoclonal antibody.

TABLE 5

Removal of residual DNA (unit: pg/ml)

Experiment 1

| | pH 7.5 | pH 6.5 | pH 5.5 |
|---|---|---|---|
| 0 h | 1142 | 624 | 113 |
| 6 h | 3288 | 1157 | 117 |

(DNA in the culture medium: 235200 pg/ml)

Experiment 2

| | pH 5.5 | pH 5.0 | pH 4.5 |
|---|---|---|---|
| 0 h | 137 | 67 | 86 |
| 6 h | 94 | 34 | 164 |

(DNA in the culture medium: 5448000 pg/ml; DNA in the unfiltered sample: 4330 pg/ml)

TABLE 6

% Recovery of humanized anti-HM1.24 antigen monoclonal antibody by filtration

| | pH 5.5 | pH 5.0 | pH 4.5 |
|---|---|---|---|
| 0 h | 98.1% | 89.6% | 87.8% |
| 6 h | 89.3% | 91.1% | 98.6% |

Although the samples purified by Protein A affinity chromatography were still rich in DNA, Experiment 1 indicated that the amount of DNA decreased with decrease in pH in the order of pH 7.5, pH 6.5 and pH 5.5, and that there was a tendency to remove more DNA at 0 hours than at 6 hours. In Experiment 2, the same experiment was carried out under conditions of pH 4.5, 5.0 and 5.5, indicating that DNA was sufficiently removed to the same extent, regardless of pH and standing period within the tested range. In addition, the calculation of % recovery indicated little loss of the humanized anti-HM1.24 antigen monoclonal antibody.

Example 4

Purification of Erythropoietin (EPO)

An EPO-containing sample (from CHO cell culture; Chugai Pharmaceutical Co., Ltd.) is used for the following examination of conditions.

Composition of EPO-Containing Sample (1 mM Phosphate Buffer);

To ensure efficient removal of residual DNA, examination is performed to determine the optimal pH for filtration through a filter. The EPO-containing sample is diluted in an acidic solution of low conductivity (2.5 mM aqueous HCl) and further converted into an acidic aqueous solution of low conductivity using 20% hydrochloric acid, followed by addition of sample DNA. The EPO-containing sample thus treated is adjusted with a 1.0 M aqueous Tris solution to the following pH level (pH=5.0 or 6.6) and then filtered through a 0.22 μm CA filter. Subsequently, DNA assay is performed on both filtered and unfiltered fractions. This examination confirms efficient reduction of DNA in the EPO-containing sample rich in DNA.

Example 5

Purification of Granulocyte Colony-Stimulating Factor (G-CSF)

A G-CSF-containing sample (from CHO cell culture; Chugai Pharmaceutical Co., Ltd.) is used for the following examination of conditions.

Composition of G-CSF-Containing Sample (20 mM Tris-HCl buffer);

To ensure efficient removal of residual DNA, examination is performed to determine the optimal pH for filtration through a filter. The G-CSF-containing sample is diluted in an acidic solution of low conductivity (2.5 mM aqueous HCl) and further converted into an acidic aqueous solution of low conductivity using 20% hydrochloric acid, followed by addition of sample DNA. The G-CSF-containing sample thus treated is adjusted with a 1.0 M aqueous Tris solution to the following pH level (pH=4.3 or 6.6) and then filtered through a 0.22 μm CA filter. Subsequently, DNA assay is performed on both filtered and unfiltered fractions. This examination confirms efficient reduction of DNA in the G-CSF-containing sample rich in DNA.

Example 6

Purification of Bovine Serum Albumin (BSA)

A BSA-containing sample is used for the following examination of conditions.

To ensure efficient removal of residual DNA, examination is performed to determine the optimal pH for filtration through a filter. The BSA-containing sample is diluted in an acidic solution of low conductivity (2.5 mM aqueous HCl) and further converted into an acidic aqueous solution of low conductivity using 20% hydrochloric acid, followed by addition of sample DNA. The BSA-containing sample thus treated is adjusted with a 1.0 M aqueous Tris solution to the following pH level (pH=4.9 or 7.5) and then filtered through a 0.22 μm CA filter. Subsequently, fractions. This examination confirms efficient reduction of DNA in the BSA-containing sample rich in DNA.

The invention claimed is:

1. A method for removing contaminant DNA in an antibody-containing sample, which comprises the followings steps:
    1) applying the antibody-containing sample to affinity chromatography on Protein A or Protein G;
    2) eluting the antibody with an acidic aqueous solution of low conductivity having a molarity of 100 mM or less;
    3) neutralizing the eluate from step (2) to form particles by addition of a buffer to raise the pH to 4 to 8, wherein the molarity of the neutralized eluate is 100 mM or less; and
    4) removing the particles to thereby remove contaminant DNA from the antibody-containing sample.

2. The method according to claim 1, wherein the acidic aqueous solution of low conductivity has a molarity of 50 mM or less.

3. The method according to claim 1, wherein the acidic solution of low conductivity is selected from the group consisting of aqueous solutions of hydrochloric acid, citric acid and acetic acid.

4. The method according to claim 3, wherein the acidic aqueous solution has a pH of 1.5 to 3.9.

5. The method according to claim 1, wherein the contaminant DNA is present at a DNA concentration of 22.5 pg/ml or less in the treated sample containing an antibody.

6. The method according to claim 1, wherein the buffer is an aqueous solution of Tris.

7. The method according to claim 1, wherein the buffer is added to raise the pH to 4.3 to 7.5.

8. The method according to claim 1, wherein the antibody is a humanized monoclonal antibody.

9. The method according to claim 8, wherein the antibody is a humanized anti-IL-6 receptor antibody.

10. The method according to claim 8, wherein the antibody is a humanized anti-HM1.24 antigen monoclonal antibody.

11. The method according to claim 8, wherein the antibody is a humanized anti-parathyroid hormone-related peptide antibody (anti-PTHrP antibody).

12. The method according to claim 8, wherein the antibody is a humanized anti-tissue factor antibody.

13. The method according to claim 1, wherein the particles are removed by filtration through a filter.

* * * * *

(12) INTER PARTES REVIEW CERTIFICATE (1839th)
United States Patent
Takeda et al.

(10) Number: US 7,332,289 K1
(45) Certificate Issued: Sep. 23, 2020

(54) METHOD OF PURIFYING PROTEIN

(75) Inventors: Kozo Takeda; Norimichi Ochi

(73) Assignee: CHUGAI SEIYAKU KABUSHIKI KAISHA

Trial Number:
IPR2017-01357 filed May 19, 2017

Inter Partes Review Certificate for:
Patent No.: 7,332,289
Issued: Feb. 19, 2008
Appl. No.: 10/471,374
Filed: Sep. 9, 2003

The results of IPR2017-01357 are reflected in this inter partes review certificate under 35 U.S.C. 318(b).

INTER PARTES REVIEW CERTIFICATE
U.S. Patent 7,332,289 K1
Trial No. IPR2017-01357
Certificate Issued Sep. 23, 2020

AS A RESULT OF THE INTER PARTES REVIEW PROCEEDING, IT HAS BEEN DETERMINED THAT:

Claims 1-8 and 13 are found patentable.

\* \* \* \* \*